United States Patent [19]

Birum

[11] 4,108,949
[45] Aug. 22, 1978

[54] O-HYDROXY (ALKOXY) PHENYLTHIOMETHYLENE DI(ORGANOPHOSPHORUS) COMPOUNDS AND PROCESS FOR MAKING SAME

[75] Inventor: Gail H. Birum, Kirkwood, Mo.

[73] Assignee: Monsanto Company, St. Louis, Mo.

[21] Appl. No.: 756,507

[22] Filed: Jan. 3, 1977

[51] Int. Cl.² ............................ C07F 9/32; C07F 9/50
[52] U.S. Cl. .......................... 260/932; 260/606.5 P; 260/968
[58] Field of Search ................ 260/932, 968, 606.5 P

[56] References Cited

U.S. PATENT DOCUMENTS

| 3,089,891 | 5/1963 | Birum | 260/931 |
| 3,183,256 | 5/1965 | Birum | 260/969 X |
| 3,257,270 | 6/1966 | Birum | 424/204 |

*Primary Examiner*—Anton H. Sutto
*Attorney, Agent, or Firm*—Herman O. Bauermeister; John D. Upham

[57] ABSTRACT

The invention relates to o-hydroxy(or alkyloxy)-phenythiomethylenedi(organophosphorus) compounds and to processes for making the same. The compounds have the general formula

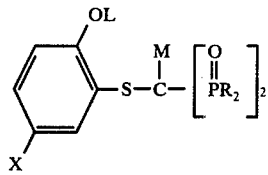

where
  L is H or R',
  R' is alkyl of 1 to 6 carbon atoms
  M is H, Cl or Br,
  X is Br, Cl, F, $CF_3$, $NO_2$, CN, $CO_2R'$, $SO_2R'$, or

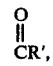

and
  R is phenyl, alkyl of 1 to 3 carbon atoms, or OR'.

The compounds of the invention have utility as corrosion inhibitors, oil additives and flame retardants.

13 Claims, No Drawings

6-HYDROXY (ALKOXY) PHENYLTHIOMETHYLENE DI(ORGANOPHOSPHORUS) COMPOUNDS AND PROCESS FOR MAKING SAME

BACKGROUND OF THE INVENTION

It was previously shown that aryl chlorodithioformates react with esters of trivalent phosphorus acids according to the following general equation (U.S. Patent No. 3,089,891):

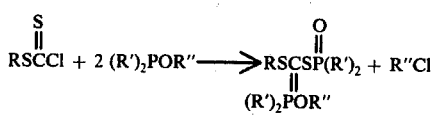

The above primary product has two organophosphorus groups, one having phosphorus bonded to the carbon atom that was initially part of the thiocarbonyl group (C=S) and the other having phosphorus bonded to the sulfur atom that was initially part of the thiocarbonyl group. There are no bond rearrangements on the aryl group of the dithioformate during the reaction.

It was further shown that products obtained according to the above equation are converted to other products by the following process (U.S. Pat. No. 3,257,270):

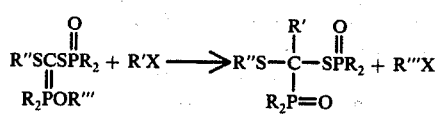

where the symbols for this equation have the meaning defined in the patent:

R is selected from the group consisting of hydrocarbyl, hydrocarbyloxy, and halohydrocarbyloxy radicals having from 1 to 6 carbon atoms; R' is selected from the group consisting of hydrogen, chlorine, bromine, and alkylthio, arylthio, and alkarylthio radicals having from 1 to 15 carbon atoms, and chlorine and bromine-substituted derivatives thereof; and R" is selected from the group consisting of phenyl, chlorophenyl, bromophenyl, and alkylphenyl radicals having from 7 to about 12 carbon atoms, and R'" is selected from the group consisting of aliphatic and halogen-substituted aliphatic radicals having from 1 to 6 carbon atoms.

Characteristic of the structures of the above products is the presence of at least two sulfur atoms, one of which is bonded to phosphorus as part of an ester of a thiophosphorus acid.

SUMMARY OF THE INVENTION

It has been found that when phenyl chloromonothioformates, having electronegative substituents, e.g. nitro, cyano, or halogen, in the para-position of the phenyl group, are treated with esters of trivalent phosphorus acids, an unusual migration of the phenyl group from oxygen to the sulfur atom of the thiocarbonyl group occurs, and two phosphorus atoms become directly bonded to the carbon atom of the thiocarbonyl group, resulting in the formation of an o-hydroxyphenylthiophosphoranylidene structure according to the general equation,

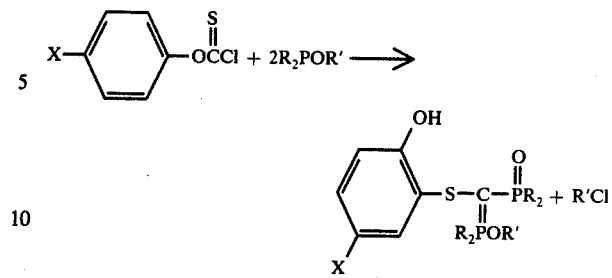

It has now been found, according to the present invention, that these o-hydroxyphenylthiophosphoranylidene products can be converted to new compounds, o-hydroxy or (alkyloxy) phenylthiomethylenedi(organophosphorus) compounds, having the general structure,

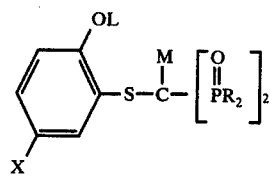

where
L is H or R',
R' is alkyl of 1 to 6 carbon atoms,
M is H, Cl, or Br,
X is Br, Cl, $CF_3$, $NO_2$, CN, $CO_2R'$, $SO_2R'$, or

CR', and
R is phenyl, alkyl of 1 to 3 carbon atoms or OR'.

Characteristic of the structure of the products of this invention are a hydroxy or alkyloxy group ortho to the sulfur atom and an electronegative group meta to the sulfur atom. Also characteristic are the presence of two identical organophosphorus groups bonded through phosphorus to the same carbon atom, neither of the phosphorus atoms being directly bonded to sulfur in contrast to the products of the references cited above.

The process of the present invention subjects the o-hydroxyphenylthiophosphoranylidene starting materials to a treatment selected from the group consisting of (a) thermal treatment at a temperature of from 125° C to 200° C.

(b) treatment with a mineral or carboxylic acid (preferably 1 to 4 carbon atoms) such as sulfuric acid, hydrochloric acid, hydrobromic acid (including anhydrous acids), formic acid, acetic acid, and trifluoroacetic acid at 0° C to 100° C.

(c) treatment with a halogen such as chlorine or bromine at a temperature of 0° C to 100° C.

In general, at least one molar proportion of the acid or halogen is used, relative to the starting material.

DETAILED DESCRIPTION OF THE INVENTION

The o-hydroxyphenylthiophosphoranylidene starting materials (I) used in the present invention are prepared in accordance with the following equation:

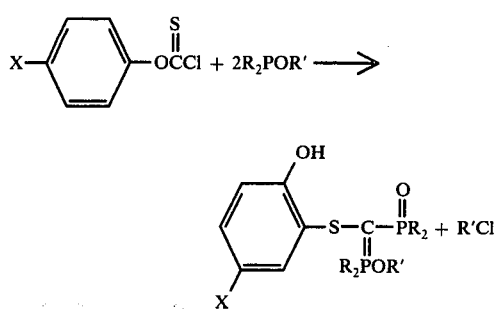

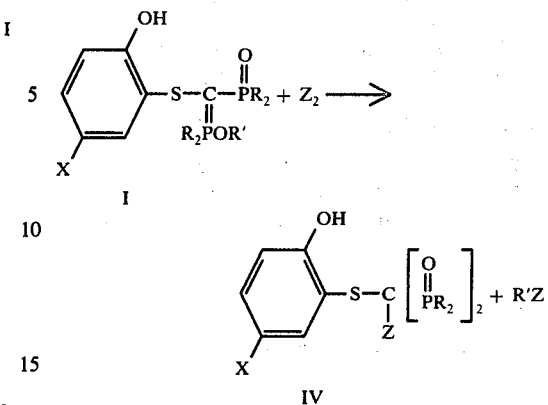

wherein Z is Br or Cl.

Trivalent phosphorus esters useful for the purpose of preparing the starting materials (I) of this invention are the phosphite, phosphonite, and phosphinite esters having at least one aliphatic radical which is bonded through an oxygen atom to the phosphorus atom and contains from 1 to 6 carbon atoms. The remaining valences of the phosphorus ester starting material may be satisfied by hydrocarbyl or hydrocarbyloxy groups having from 1 to 6 carbon atoms. Phosphite esters are preferred for reasons of economy and ready availability. However, the phosphonite and phosphinite esters may also be used. Alkyl phosphites useful for the preparation of the starting materials are the simple or mixed trialkyl phosphites such as trimethyl, triethyl, tri-n-propyl, triisopropyl, tri-n-butyl, triisoamyl, trihexyl, dimethyl ethyl and di-n-propyl methyl phosphites.

Phosphonite esters having at least one aliphatic radical bonded through oxygen to the phosphorus atom will also react to provide starting materials of the invention. Examples of phosphonite esters that may be used are the simple or mixed alkyl phosphonites, e.g. dimethyl methyl-, diethyl ethyl-, di-n-propyl propyl-, and the ethyl hexyl butylphosphonites; dimethyl phenyl-, diethyl phenyl-, and dibutyl phenylphosphonite.

Although less commonly available at the present time, phosphinite esters may also be used to prepare starting materials of the present invention. Such phosphinite esters useful in this invention are those having organic radicals the same as those described above in more detail for the phosphite and phosphonite esters. However, for purposes of illustration, a few examples of phosphinite esters useful in this invention are ethyl dimethyl-, butyl dimethyl-, methyl diphenyl-, and ethyl diphenylphosphinite.

Phenyl chlorothionoformates that are used to react with any of the above esters of trivalent phosphorus acids to prepare starting materials of this invention are those having an electronegative substituent in the para-position of the phenyl group, e.g., p-bromophenyl, p-chlorophenyl, p-fluorophenyl, p-nitro-phenyl, p-cyanophenyl, p-methoxycarbonylphenyl, p-ethyl-sulfonylphenyl, and p-propionylphenyl chlorothionoformates.

Reaction of esters of trivalent phosphorus acids with the para-substituted phenyl chlorothionoformates occurs within the range of about 0° to 100° C, preferably at 10° to 70° C. Although cooling is not necessary, it is usually preferred to apply some cooling, particularly when using larger quantities of reactants, for example, where the symbols are the same as above.

The products of general structure I are chemically reactive and readily converted to new structures of the present invention, for example, to structure II by a thermal rearrangement promoted by heating at 125° C to 200° C.

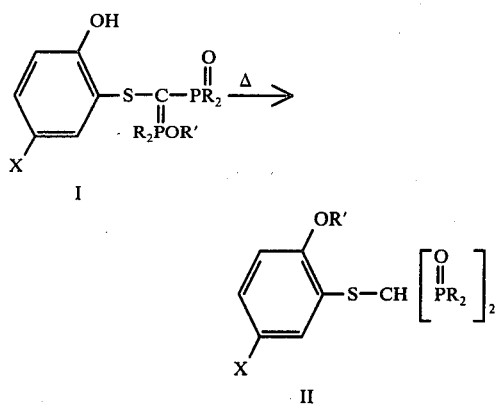

Products of general structure I are converted to structure III by the treatment of I with hydrogen acids, HY, e.g. mineral and carboxylic acids (1 to 4 carbon atoms) such as hydrochloric, sulfuric, and trifluoroacetic acids according to the following equation:

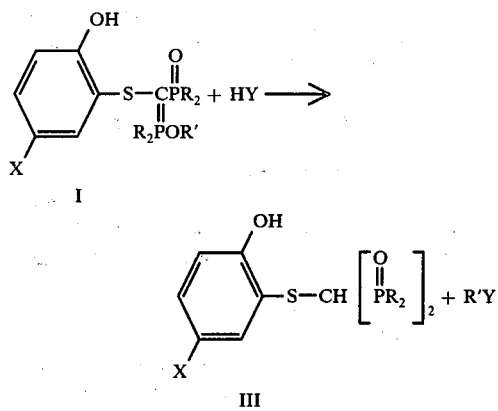

A third type of new product that is derived from Compound I has Structure IV. This conversion is made by the treatment of I with chlorine or bromine at 0° C to 100° C as in the following equation:

more than about 0.5 mole of the trivalent phosphorus ester reactant. Reaction may be complete at ordinary temperatures or below, but it is usually preferred to apply external heating after the initial exothermic reaction has subsided. The use of an inert solvent or diluent may be advantageous, particularly when employing higher molecular weight reactants. Such solvents may be, for example, methylene chloride, benzene, toluene, hexane, cyclohexane, ether, and chlorobenzene.

The above conditions are also applicable to the present treatments, e.g. thermal treatment, reaction with an acid, and reaction with a halogen.

The following examples illustrate specific embodiments of the invention but are not limitative of the scope of the invention.

EXAMPLE 1

Preparation of the compound,

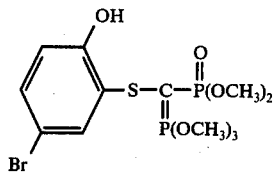

I

A solution of 27.3g. (0.22m.) of trimethyl phosphite in 50g. of benzene is stirred under nitrogen and cooled at 15°–20° C. as 25.1g. (0.10m.) of 4-bromophenyl chlorothionoformate is added dropwise in 0.2 hr. When the cooling bath is removed the temperature increases slowly to 48° C. The reaction mixtue is then warmed at reflux for one-half hour and allowed to cool. Filtration gives 20.8g. of white solid, mp 143°–145° (from acetonitrile), which is dimethyl (5-bromo-2-hydroxyphenylthio)(trimethoxyphosphoranylidene)methylphosphonate(I), $^{31}$P nmr (DMSO-d$_6$)—52.0ppm(d of m,J$_{PP}$=132Hz, J$_{PH}$=11Hz),—30.0ppm (d of m, J$_{PP}$=132Hz, J$_{PH}$=11Hz) (1:1 areas); $^1$H nmr δ 10.0 (s,1,OH), δ 7.4(d,1,J$_{H_6-H_4}$=2H$_z$), δ 7.0(d of d,1,J$_{H_4-H_3}$=8Hz), δ 6.6 (d,1,J$_{H_3-H_4}$=8Hx), δ 3.8(d,9,J=11 Hz), δ 3.5(d,6,J=11Hz); mass spectrum M$^+$ = 448 and 450;

Anal. Calcd for C$_{12}$H$_{19}$BrO$_7$P$_2$S: C, 32.08; H, 4.26; Br, 17.79; P, 13.79; S, 7.14. Found: C, 32.25; H, 4.31; Br, 17.82; P, 13.67; S, 7.40.

When a portion of product I is warmed at 170° to 190° C in o-dichlorobenzene, it rearranges to a new product, $^{31}$P nmr —19.2 ppm, which is tetramethyl (5-bromo-2-methoxyphenylthio)methylenediphosphonate (II).

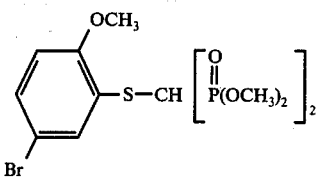

II

The treatment of a solution of product I in benzene with anhydrous hydrogen chloride at 20°–30°, followed by stripping to 60°/1 mm, gives tetramethyl (5-bromo-2-phenylthio)methylenediphosphonate (III), $^{31}$P nmr —19.7 ppm.

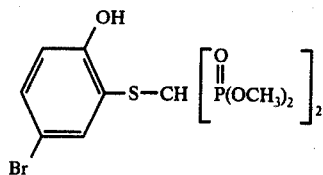

III

The treatment of a solution of 2.0g of I in 15 ml of benzene with 0.7g of phenylisocyanate and two drops of pyridine, followed by warming to 80° and then cooling, gives 1.9g of white solid (IV), mp 155°–157° C; $^{31}$P nmr (DMSO-d$_6$) —51.7 ppm (d,J$_{P-P}$=129Hz), —28.6 ppm (d,J$_{PP}$=129Hz) (1:1 areas).

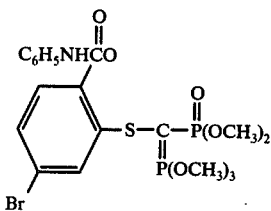

IV

Anal. Calcd. for C$_{19}$H$_{24}$BrNO$_8$P$_2$S: Br, 14.06; N, 2.46; P, 10.90; S, 5.64. Found: Br, 14.32; N, 2.44; P, 10.74; S, 5.71.

The addition of trifluroacetic acid to a solution of IV gives product V, $^{31}$P nmr (DMSO-d$_6$)—18.8 ppm.

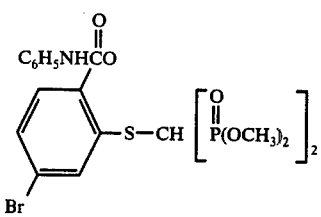

V

EXAMPLE 2

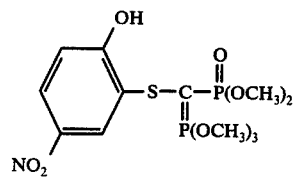

I

A solution of 43.5g (0.2m.) of 4-nitrophenyl chlorothionoformate in 125 g of benzene is stirred and cooled at —10° C. as 62.0g (0.5m.) of freshly distilled trimethyl phosphite is added. When this mixture is allowed to warm, solid begins to form at about 0° C and heat of reaction is noticeable. The temperature is kept below 20° until heat of reaction diminishes and then the slurry is warmed at 40°–45° C for one hour. Filtration gives 70.7g (85% yield) of yellow solid, dimethyl (2-hydroxy-5-nitrophenylthio)(trimethoxyphosphoranyidene)methylphosphonate (I), mp 183°–185°.

Instead of beginning with the nitro-substituted starting material the use of the trifluoromethyl group, the cyano group, or the methylcarbyloxy group, or the propylsulfonyl group, or the methylacyl group give similar products in the present invention.

A 20.7g (0.05m.) portion of I is stirred in 60g of benzene as 6.0g (0.05m.) of trifluoroacetic is added rapidly at 25°–30° C. This mixture is warmed to reflux and then filtered while warm, giving 18.0g of tetramethyl (2-hydroxy-5-nitrophenylthio)methylenediphosphonate (III), a white solid; mp 106°–111° (from benzene); $^{31}$P nmr (DMSO-d$_6$)−19.6 ppm; 'H nmr δ 11.8(s,1,OH), δ 8.3(d,1,J$_{H_6-H_4}$=3Hz), δ 8.0(d of d,1,J$_{H_4-H_6}$=3Hz), J$_{H_4-H_3}$=9Hz), δ 7.0(d,1,J$_{H_3-H_4}$=9Hz), δ 4.5(t,1,J$_{H-PP}$=21Hz), δ 3.7(d,12,J$_{PP-CH_3}$=11); mol. wgt. 410(acetone), theory 401.

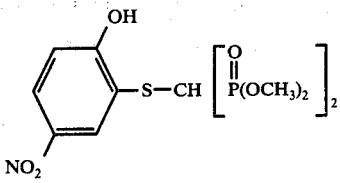

III

Anal. Calcd. for C$_{11}$H$_{17}$NO$_9$P$_2$S: C, 32.92; H, 4.27; N, 3.49; P, 15.44; S, 7.99. Found: C, 33.08; H, 4.20; N, 3.41; P, 15.38; S, 8.03.

A mixture of 15.0g of I and 20 g of o-dichlorobenzene is stirred and warmed, giving a clear solution at about 160° C. Warming is continued at 180° for 0.25 hr. The reaction mixture is refrigerated for one hour, and then it is filtered and the solid is recrystallized from benzene, giving 6.3g of tetramethyl (2-methoxy-5-nitrophenylthio)methylenediphosphonate (II); mp 118°–119°; $^{31}$P nmr (dMSO-d$_6$)−19.1 ppm; H nmr δ 8.40 (d,1, J$_{H_6-H_4}$=2.5Hz), δ 8.18(d of d,1,J$_{H_4-H_6}$=2.5Hz, J$_{H_4-H_3}$=9.5Hz), δ 7.24(d,1,J$_{H_3-H_4}$=9.5Hz), δ 4.6(t,1,J$_{H-PP}$=21Hz), δ 4.03 (s,3,arylOCH$_3$), δ 3.76(d,12,J$_{CH_3OP}$=11Hz); mol. wgt. 420 (acetone), theory 415.

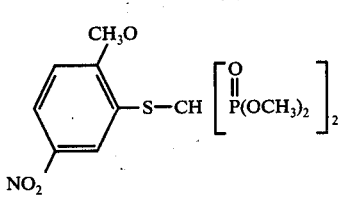

II

Anal. Calcd. for C$_{12}$H$_{19}$NO$_9$P$_2$S: C, 34.69; H, 4.61; N, 3.37; P, 14.92; S, 7.72. Found: C, 34.60; H, 4.54; N, 3.35; P, 14.77; S, 7.62.

A mixture of 15.0g of I and 30g of concentrated hydrochloric acid is warmed at reflux for 20 hrs, and then the reaction mixture is evaporated to dryness. The residue is broken up and extracted five times with warm benzene and dried, giving 10.6g of (2-hydroxy-5-nitrophenylthio)methylenediphosphonic acid (IV), a yellow solid; mp 190°–195°(dec.);$^{31}$P nmr (DMSO-d$_6$) −13.8 ppm (d,J$_{PP-H}$=20Hz); 'H nmr 11.7(s,5,OH), δ 8.4(d,1, 8.1 (d of d,1), δ 7.1 (d,1), δ 3.6(t,1,J$_{H-PP}$=20Hz).

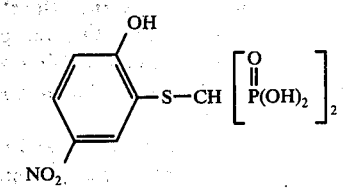

IV

The treatment of a solution of I in methylene chloride with an equimolar amount of bromine while stirring and cooling produces tetramethyl [(bromo)(2-hydroxy-5-nitrophenyltnio)methylene]diphosphonate,

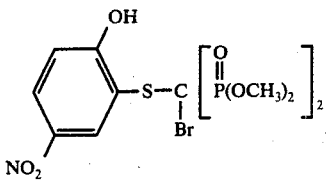

IV

EXAMPLE 3

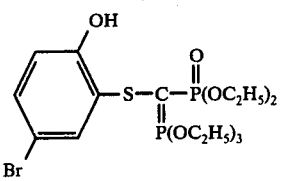

I

A solution of 72.8g (0.44m.) of triethyl phosphite in 100g. of cyclohexane is stirred and cooled as 52.5g (0.21m.) of 4-bromophenyl chlorothionoformate is added in 0.25 hr at 35°–40° C. The reaction mixture is then warmed to 70°, cooled, and filtered under nitrogen, giving 67.2g (62% yield) of diethyl (5-bromo-2-hydroxyphenylthio)(triethoxyphosphoranylidene)-methylphosphonate (I), a white solid, mp 118°–120° (from benzenecyclohexane), $^{31}$P nmr (DMSO-d$_6$)−47.1 ppm(d,J$_{P-P}$=122Hz),−32.9 ppm (d,J$_{PP}$=122Hz)(1:1 areas).

Anal. Calcd. for C$_{17}$H$_{29}$BrP$_2$O$_7$S; C,39.31; H, 5.63; Br, 15.38, P, 11.93; S, 6.17. Found: C, 39.27; H, 5.80; Br, 15.47; P, 11.61; S, 5.99.

Treatment of a solution of I in methylene chloride with excess anhydrous hydrogen chloride at 1°–4° followed by warming to 25° and stripping of solvent gives a viscous syrup. Crystallization from cyclohexane gives white solid III, $^{31}$P nmr −18.4 ppm (d,J$_{P-H}$=17Hz).

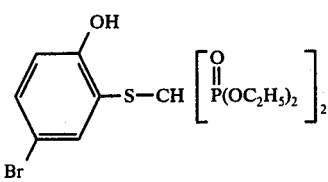

III

A 2.0g portion of III and 1.5g of 4-nitrophenylisocyanate are stirred in 15 ml of benzene as four drops of pyridine are added. This mixture is warmed to reflux, cooled, and filtered. The filtrate is stripped of solvent, and the residue is recrystallized twice from benzene, giving yellow solid, mp 156°–159° C, $^{31}$P nmr (SMSO-d$_6$)−16.8 ppm.

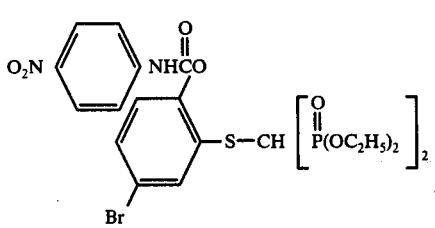

Anal. Calcd. for $C_{22}H_{29}BrN_2O_{10}P_2S$: Br,12.19; N, 4.27; P, 9.45; S, 4.89. Found: Br, 12.48; N, 4.27; P, 9.20; S, 4.89.

The treatment of a solution of I in methylene chloride with an equimolar amount of chlorine while stirring and cooling produces tetraethyl[(5-bromo-2-hydroxyphenylthio)(chloro)-methylene]diphosphonate,

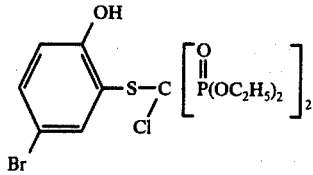

IV

EXAMPLE 4

Preparation of

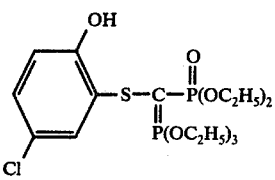

I

A solution of 136g(0.82m.) of freshly distilled triethyl phosphite in 200 ml of benzene is stirred and cooled as 82.8g (0.40m.) of 4-chlorophenyl chlorothionoformate is added in 0.3 hr at 25°-35° C. White solid forms during this addition. The reaction mixture is warmed at 60°-82° for 0.5 hr and then cooled and filtered, giving 115g of diethyl (5-chloro-2-hydroxyphenylthio)(triethoxyphosphoranylidene)methylphosphonate (I); mp 127°-128° (from toluene); $^{31}P$ nmr (CHCl$_3$) —47.9 ppm (d,J$_{P-P}$=128Hz), —31.1ppm (d,J$_{PP}$=128Hz; mol. wgt. 469 (CHCl$_3$), theory 475.

Anal. Calcd. for $C_{17}H_{29}O_7P_2ClS$: C, 43.00; H, 6.16; Cl, 7.47; P, 13.05; S, 6.74. Found: C, 43.22; H, 6.16; Cl, 7.53; P, 13.04; S, 6.60.

A 35.6g (0.075m.) portion of I is dissolved in 150 ml of methylene chloride, and the solution is stirred and cooled as anhydrous hydrogen chloride is added sub-surface at 2°-5° C until the solution is saturated. The reaction mixture is stripped of solvent at reduced pressure, and the residue is recrystallized from benzene-hexane, giving 20g of tetraethyl (5-chloro-2-hydroxyphenylthio)methylenediphosphonate III); mp 87°-88° C; $^{31}P$ nmr —18.0 ppm (d,J$_{PP-H}$=15Hz).

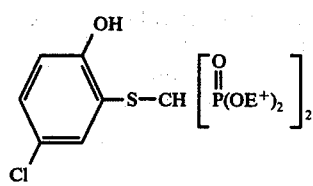

III

Anal. Calcd. for $C_{15}H_{25}ClO_7P_2S$: C, 40.31; H, 5.64; Cl, 7.94; P, 13.86; S, 7.18. Found: C, 40.47; H, 5.76; Cl, 8.04; P, 13.97; S, 7.15.

When a mixture of 16.0g of I and 59.0g of 37% aqueous hydrogen chloride is warmed at 70°-105° C for 2 hrs, and the reaction mixture is then evaporated to dryness, the residue contains (5-chloro-2-hydroxyphenyl- thio)methylenediphosphonic acid, $^{31}P$ nmr —16.6 ppm.

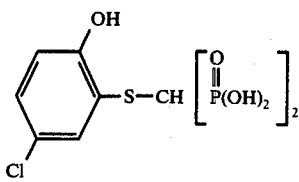

When a solution of 15g of I in 30g of o-dichlorobenzene is warmed at 175°-185° C. for 0.25 hr, the reaction mixture contains tetraethyl (5-chloro-2-ethoxyphenylthio) methylenediphosphonate (II).

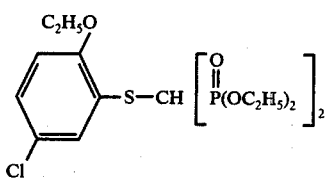

II

A solution of 18.0g (0.038m.) of I in 200 ml of methylene chloride is stirred and cooled as 3.2g (0.045 m.) of chlorine is added sub-surface in 0.1 hr at 4°-9° C. Stripping of the solvent to 90°/1mm gives 18.2g (100% yield) of tetraethyl (chloro)(5-chloro-2-hydroxyphenylthio)-methylenediphosphonate (IV), a viscous, colorless oil, $^{31}P$ nmr —13.0 ppm.

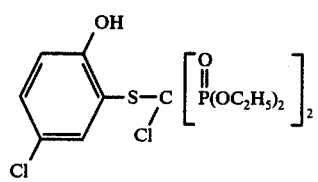

IV

EXAMPLE 5

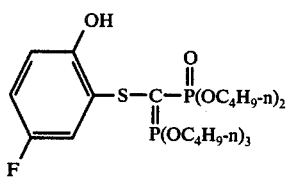

I

When 1.0 mole of 4-fluorophenyl chlorothionoformate is added to 2.0 moles of tri(n-butyl) phosphite in benzene, and the solution is warmed and then stripped of solvent, the residue contains dibutyl (5-fluoro-2-hydroxyphenylthio)(tributoxyphosphoranylidene)methylphosphonate (I).

Treatment of a portion of (I) in methylene chloride with anhydrous hydrogenchloride produces tetrabutyl (5-fluoro-2-hydroxyphenylthio)methylenediphosphonate (III).

When a solution of (I) in o-dichlorobenzene is warmed at 175°-185°, the reaction mixture contains tetrabutyl (2-butoxy-5-fluorophenylthio)methylenediphosphonate (II).

EXAMPLE 6

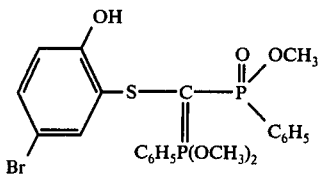

4-Bromophenyl chlorothionoformate, 25.1g (0.1m.) is added to a solution of 34.0g (0.2 m.) of dimethyl phenylphosphonite in 150 ml. of benzene with cooling at 20°-25°. The reaction mixture is warmed to 80° and then stripped at reduced pressure. The residue is extracted with cyclohexane, and the insoluble portion is crystallized from acrylonitrile, giving 39.2g. of methyl [(5-bromo-2-hydroxyphenylthio)(dimethoxyphenyl-phosphoranylidene)-methyl]phenylphosphinate(I), a white solid; mp 159°-160°; $^{31}$P nmr (CDCl$_3$) −63.5 ppm (d,J$_{P-P}$=93Hz), −43.2 ppm (d,J$_{P-P}$=93Hz); mol. wgt. 550 (CHCl$_3$), theory 541; M$^+$ 540 (mass spectrum).

Anal. Calcd. for C$_{22}$H$_{23}$BrO$_5$P$_2$S: C, 48.81; H, 4.28; Br, 14.76; P, 11.44; S, 5.92. Found: C, 49.88; H, 4.31; Br, 14.25; P, 10.69; S, 5.61.

When a 10.2g (0.02m.) portion of I in 150 ml of acetonitrile is treated with 2.5g (0.022m.) of trifluoroacetic acid, and the reaction mixture is stripped of solvent, a viscous gum is obtained which contains (5-bromo-2-hydroxyphenylthio)methylenebis(methyl phenylphosphinate)(III), $^{31}$Pnmr (DMSO-d$_6$) −35.4 ppm.

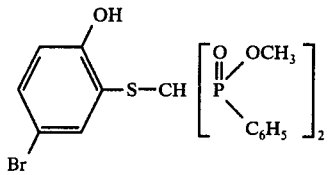

When a solution of I in o-dichlorobenzene is warmed at 180°-185° C., in intramolecular rearrangement occurs, giving (5-bromo-2-ethoxyphenylthio)methylene bis(methyl phenylphosphinate)(II)

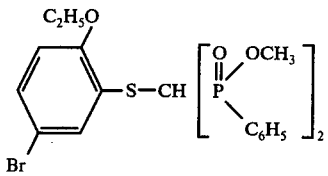

EXAMPLE 7

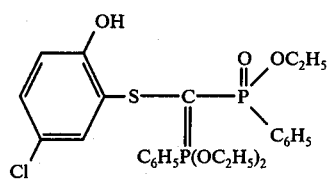

p-Chlorophenyl chlorothionoformate, 62.2g. (0.30 mole), is added to a solution of 63.5g. (0.32 mole) of diethyl phenylphosphonite in 250 ml. of benzene in 0.2 hour with cooling at 15°-30° C. There is heat of reaction during only about the first half of the addition, indicating that two moles of the phosphonite is reacting with one mole of the chlorothionoformate.

A white solid separates early in the addition. An additional 55.5g. (0.28 mole) of diethyl phenylphosphonite (total, 0.60 mole) is then added in 0.1 hour with cooling at 25°-32° C. The reaction mixture is warmed to reflux and the solid allowed to crystallize to give 106.5g (66% yield) of ethyl [(5-chloro-2-hydroxyphenylthio)(-diethoxyphenylphosphoranylidene) methyl]phenylphosphinate (I), a white solid; mp 165°-166° C; $^{31}$P nmr (CHCl$_3$) −60.9 ppm (d,J$_{P-P}$=92Hz), −41.6 ppm (d,J$_{PP}$=92Hz).

Anal. Calcd. for C$_{25}$H$_{29}$ClO$_5$P$_2$S: C, 55.71; H, 5.42; Cl, 6.58; P, 11.49; S, 5.95. Found: C, 55.89; H, 5.59; Cl, 6.52; P, 11.30; S, 6.08.

When a portion of I in methylene chloride is stirred and cooled as an equimolar amount of bromine is added subsurface, (bromo)(5-chloro-2-hydroxyphenylthio)-methylenebis (ethyl phenylphosphinate) (IV) is formed.

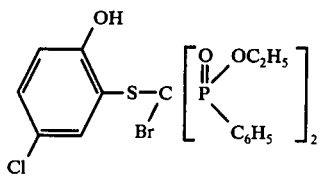

EXAMPLE 8

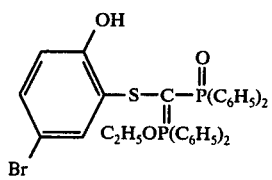

The addition of 25.1g(0.1m.) of 4-bromophenyl chlorothionoformate to a solution of 46.0g(0.2m.) of ethyl diphenylphosphinite in 300 ml of benzene with cooling at 25°-30° C results in immediate separation of a white solid. The white slurry is warmed to 65°, cooled, filtered, and the solid washed with benzene and with acetonitrile, giving [(5-bromo-2-hydroxyphenylthio)(diphenylethoxyphosphoranylidene)methyl]diphenylphosphine oxide (I), a white solid, insoluble in DMSO.

One-third of I is stirred in acetonitrile as 10g of trifluroacetic acid is added. Solid I dissolves and then another white solid separates during this addition. Recrystallization from acetonitrile gives (5-bromo-2-hydroxyphenylthio)methylenebis(diphenylphosphine oxide) (III), white solid; mp 183°-185.5°; $^{31}$P nmr (DMSO-d$_6$) −29.8ppm; $^1$H nmr δ 11.0(s,1,OH), δ 5.5(t,1,J$_{H-PP}$=13Hz), and aryl protons.

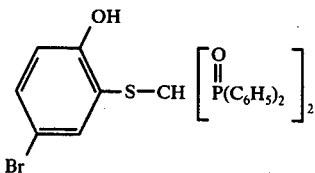

Anal. Calcd. for C$_{31}$H$_{25}$BrO$_3$P$_2$S: C, 60.10; H, 4.07; Br, 12.90; P, 10.00; S, 5.18. Found: C, 60.02; H, 4.13; Br, 13.03; P, 9.94; S, 5.14.

When a solution of I in o-dichlorobenzene is warmed to 175°–180° C, the reaction mixture contains [(5-bromo-2-ethoxyphenylthio)methylene]bis(diphenylphosphine oxide),

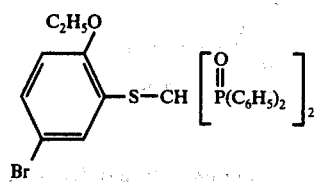

EXAMPLE 9

Preparation of the compound,

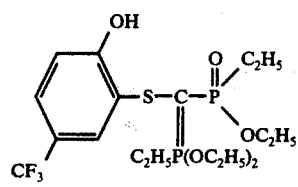

When 4-(trifluoromethyl)phenyl chlorothionoformate is treated with diethyl ethylphosphonite at a 1:2 molar ratio in benzene, an exothermic reaction occurs, forming ethyl [(2-hydroxy-5-trifluoromethylphenylthio)(diethoxyethylphosphoranylidene)methyl]ethylphosphinate (I).

The treatment of a portion of I in methylene chloride with anhydrous HBr produces (2-hydroxy-5-trifluoromethylthio)methylenebis(ethyl ethylphosphinate),

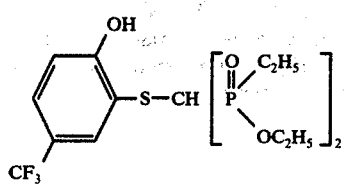

When a portion of I dissolved in o-dichlorobenzene is warmed at 170°–190° C for 0.5 hr., (2-ethoxy-5-trifluoromethylphenylthio)methylenebis(ethyl ethylphosphinate) (II) is produced.

The treatment of a solution of I is methylene chloride with chlorine gives as the major product (chloro)(2-hydroxy-5-trifluoromethylphenylthio)methylenebis-(ethyl ethylphosphinate),

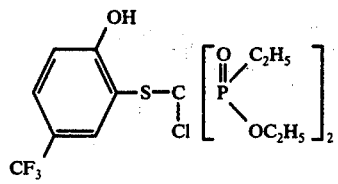

EXAMPLE 10

Preparation of the compound

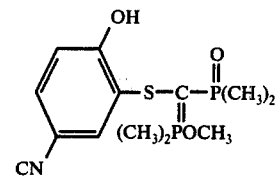

The treatment of a solution of 4-cyanophenyl chlorotrionoformate in toluene with methyl dimethylphosphinite at a 1:2 molar ratio produces [(5-cyano-2-hydroxyphenylthio)-(dimethylmethoxyphosphoranylidene)methyl]dimethylphosphine oxide (I).

When a solution of I in o-dichlorobenzene is warmed at 160°–185° for 0.75 hr., an intramolecular rearrangement occurs, resulting in the formation of (5-cyano-2-methoxyphenylthio)methylenebis(dimethylphosphine oxide),

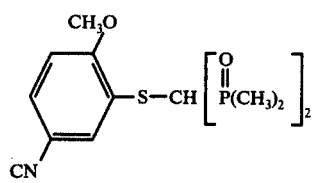

EXAMPLE 11

The products of the present invention are useful as corrosion inhibitors, lubricating oil additives and are flame retardants.

In corrosion inhibition, for example in aqueous cooling solutions, or in lubricating oils, the phosphorus compounds of the invention are used at 0.1 to 5 wt. % based upon the total mixture. For example Compound II of Example 1, or Compound III of Example 5 is used at 1 wt. % concentration to reduce corrosion of metal surfaces such as iron. In lubricating oils, both natural, and of the synthetic ester type, the present phosphorus compounds at 0.01 5 wt. % are useful as dispersants for the detergents, extreme pressure agents, viscosity index modifiers and other additives commonly used in oils. As an example, 0.5 wt. % of Compound II of Example IV, or Compound III of Example 6 used in a hydrocarbon lubricating oil base are useful as a dispersants.

For flame retardant purposes, the phosphorus compounds are used with polymeric substrates such as polyesters, e.g. polyethylene terephthalate, and nylons, such as nylon-6,6. Other polymers and resins include polyurethanes, and vinyl polymers such as acrylonitrile. The phosphorus compound additive of the invention are used at concentrations of 1.0 wt. % to 20 wt. % based upon the total mixture. The additives, e.g., Compound III of Example I or Compound III of Example 6, or Compound II of Example 8 are applied to the finished polymer as a coating or dipping treatment from a solvent dispersion such as water, or may be added to the starting components before polymerization.

What is claimed is:

1. As a composition of matter,

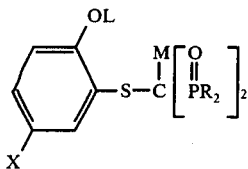

where
L is H or R',
R' is alkyl of 1 to 6 carbon atoms,
M is H, Cl or Br
X is Br, Cl, F, $CF_3$, $NO_2$, CN, $CO_2R'$, $SO_2R'$, or

and
R is phenyl, alkyl of 1 to 3 carbon atoms, or $OR'$.

2. As a composition of matter

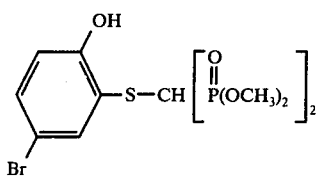

tetramethyl (5-bromo-2-hydroxyphenylthio)methylenediphosphonate.

3. As a composition of matter tetraethyl (5-bromo-2-hydroxyphenylthio)methylenediphosphonate.

4. As a composition of matter tetramethyl (5-bromo-2-methoxyphenylthio)methylenediphosphonate.

5. Process for the preparation of tetramethyl-(5-bromo-2-methoxyphenylthio)methylenediphosphonate which comprises heating the compound

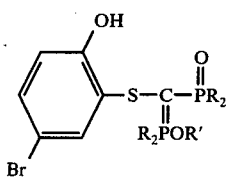

at a temperature of 125° C to 200° C.

6. Process for preparation of

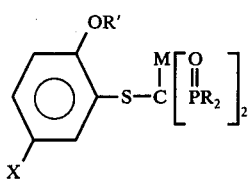

where
R' is alkyl of 1 to 6 carbon atoms
M is H, Cl or Br
X is Br, Cl, F, $CF_3$, $NO_2$, CN, $CO_2R'$, or

and

R is phenyl, alkyl of 1 to 3 carbon atoms, or R' which comprises subjecting a compound having the formula

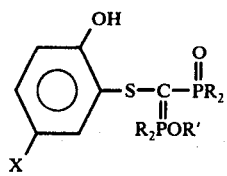

to thermal treatment at a temperature of from 125° C to 200° C.

7. Process for preparation of tetramethyl(2-methoxy-5-nitrophenylthio)methylenediphosphonate which comprises heating the compound

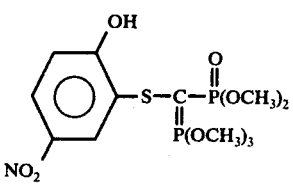

at a temperature of 125° C to 200° C.

8. Process for preparation of tetraethyl (5-chloro-2-ethoxyphenylthio)methylenediphosphonate which comprises heating the compound

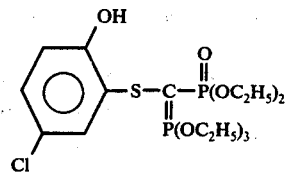

at a temperature of 125° C to 200° C.

9. Process for preparation of tetrabutyl (2-butoxy-5-fluorophenylthio)methylenediphosphonate which comprises heating the compound

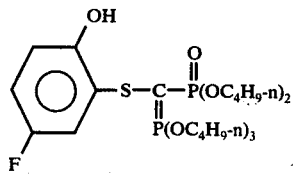

at a temperature of 125° C to 200° C.

10. Process for preparation of (5-bromo-2-ethoxyphenylthio)methylenebis(methyl phenylphosphinate) which comprises heating the compound

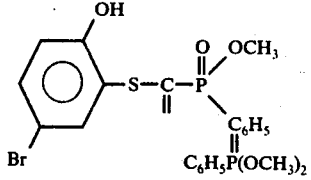

at a temperature of 125° C to 200° C.

11. Process for preparation of [(5-bromo-2-ethoxyphenylthio)methylene]bis(diphenylphosphine oxide) which comprises heating the compound 12. Process for preparation of (2-ethoxy-5-trifluoromethylphenylthio)methylenebis(ethyl ethylphosphinate) which comprises heating the compound
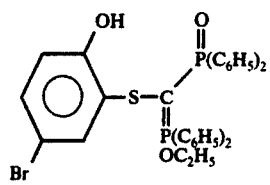
at a temperature of 125° C to 200° C.
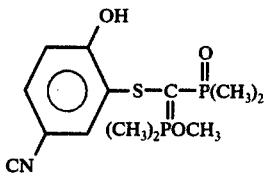
at a temperature of 125° C to 200° C.
13. Process for preparation of (5-cyano-2-methoxyphenylthio)methylenebis(dimethylphosphine oxide) which comprises heating the compound
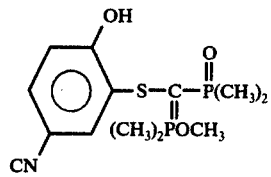
at a temperature of 125° C to 200° C.
* * * * *